United States Patent
Beilfuss et al.

(10) Patent No.: US 8,895,043 B2
(45) Date of Patent: *Nov. 25, 2014

(54) REDUCING FORMALDEHYDE EMISSIONS IN FORMAL-CONTAINING COMPOSITIONS

(71) Applicant: Air Liquide Sante (International), Paris (FR)

(72) Inventors: Wolfgang Beilfuss, Hamburg (DE); Ralf Gradtke, Tornesch (DE); Ingo Krull, Tangstedt (DE); Klaus Weber, Hamburg (DE)

(73) Assignee: Air Liquide Sante (International), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/036,419

(22) Filed: Sep. 25, 2013

(65) Prior Publication Data

US 2014/0024689 A1    Jan. 23, 2014

Related U.S. Application Data

(62) Division of application No. 10/663,257, filed on Sep. 16, 2003, now Pat. No. 8,568,754.

(30) Foreign Application Priority Data

Sep. 24, 2002 (DE) .................... 102 44 442

(51) Int. Cl.
- *A01N 25/00* (2006.01)
- *A01N 25/32* (2006.01)
- *A01N 43/76* (2006.01)
- *A01N 47/28* (2006.01)

(52) U.S. Cl.
CPC .............. *A01N 25/00* (2013.01); *A01N 43/76* (2013.01); *A01N 47/28* (2013.01)
USPC .......................................... 424/405; 424/406

(58) Field of Classification Search
None
See application file for complete search history.

(56) References Cited

U.S. PATENT DOCUMENTS

| | | | |
|---|---|---|---|
| 4,148,905 A | 4/1979 | Eggensperger et al. | |
| 4,166,122 A | 8/1979 | Paulus et al. | |
| 4,452,780 A | 6/1984 | Ecanow | |
| 4,655,815 A | 4/1987 | Jakubowski | |
| 5,037,843 A | 8/1991 | Schoenberg | |
| 5,332,765 A | 7/1994 | Lorentzen et al. | |
| 5,428,050 A | 6/1995 | Merianos | |
| 5,496,842 A | 3/1996 | Merianos | |
| 5,616,722 A | 4/1997 | Schoenberg et al. | |
| 5,670,160 A | 9/1997 | Eggensperger et al. | |
| 5,684,118 A | 11/1997 | Breyer et al. | |
| 6,348,483 B1 | 2/2002 | Beilfuss et al. | |
| 6,355,679 B1 | 3/2002 | Beilfuss et al. | |
| 6,469,060 B2 | 10/2002 | Beilfuss et al. | |
| 7,078,005 B2 | 7/2006 | Smith et al. | |
| 8,329,063 B2 * | 12/2012 | Beilfuss et al. | ............... 252/380 |
| 2001/0021711 A1 | 9/2001 | Beilfuss et al. | |
| 2004/0151742 A1 * | 8/2004 | Beilfuss et al. | ............... 424/400 |

FOREIGN PATENT DOCUMENTS

| | | |
|---|---|---|
| DE | 1183632 | 12/1964 |
| DE | 4026756 | 2/1992 |
| DE | 4141953 | 6/1993 |
| DE | 4242082 | 6/1994 |
| DE | 19722858 | 11/1998 |
| DE | 19842116 | 3/2000 |
| DE | 199961621 | 7/2001 |
| EP | 0060471 | 9/1982 |
| EP | 0327220 | 1/1989 |
| GB | 2274779 | 2/1993 |
| JP | 02169501 A * | 6/1990 |
| RO | 108290 | 4/1994 |
| RU | 2026336 | 1/1995 |
| WO | 9852416 | 11/1998 |
| WO | 0141570 | 6/2001 |

OTHER PUBLICATIONS

Grotan BK informational page accessed online on Aug. 26, 2010 at http://www.chemindustry.com/chemicals/0475446.html. 1 page.

* cited by examiner

*Primary Examiner* — Carlos Azpuru
*Assistant Examiner* — Casey Hagopian
(74) *Attorney, Agent, or Firm* — Young & Thompson

(57) ABSTRACT

Method for reducing the formaldehyde emission of a composition containing a formal by adding urea, urea derivatives, amino acids, guanidine or guanidine derivatives.

6 Claims, No Drawings

REDUCING FORMALDEHYDE EMISSIONS IN FORMAL-CONTAINING COMPOSITIONS

The present invention relates to a preservative with reduced formaldehyde emission, and to the preparation and use thereof.

Formaldehyde donor compounds, for example O-formals and N-formals, are used as biocides in a series of products and preparations for reducing microbial growth. A series of documents is known which describe the use of O-formals and N-formals.

DE-42 42 082 A1 discloses hydrolyzable polymeric resins and binders for antifouling paints. As well as hydrolyzable polymeric resin, the binder system can also comprise cobiocides, such as dichlorophenyl-dimethylurea or 2-methylthio-4-tert-butylamino-6-cyclo-propylamino-s-triazine.

U.S. Pat. No. 4,655,815 discloses a synergistic antimicrobial mixture of 2-bromo-2-bromomethylglutaronitrile and formaldehyde donor. Examples of formaldehyde donors are 2-[(hydroxymethyl)amino]-2-methylpropanol, 2-hydroxyethyl-2-nitro-1,3-propanediol, mixtures of 5-hydroxy-methyl-1-aza-3,7-dioxabicyclo-(3.3.0)octane, 2-[(hydroxymethyl)amino]ethanol, 1-(3-chloroallyl)-3,5,7-triaza-1-azoniaadamantane chloride, N-(3-chloroallyl)heximinium chloride, hexamethylenetetramine(hexamine) halohydrocarbon quats and dimethyloldimethylhydantoin.

GB-2 274 779 A discloses a microbicidal formulation which consists of a mixture of a sulphur-containing aromatic compound and a triazine compound, dissolved in a solvent. The sulphur-containing aromatic compound can, for example, be an isothiazolone derivative, the thiazine compound may be 2,2',2"-(hexahydro-1,3,5-triazine-1,3,5-triyl) triethanol (triazinetriethanol, Grotan BK).

EP-0 327 220 B1 describes a synergistic combination of selected formaldehyde donor with iodopropargyl compound. The disclosed compositions comprise, as preferred iodopropargyl compound, iodopropynyl butyl-carbamate (IPBC) and, as formaldehyde donors, nontoxic and odour-free compounds which are suitable for use in bodycare compositions. Examples of formaldehyde donors are imidazolidinylurea (=Germall 115=N,N"-methylene-bis(N'-(3-hydroxymethyl)-2,5-dioxoimidazolidin-4-yl)urea), diazolidinylurea (=imidazolidinylurea II=Germall II=1-(1,3-bis(hydroxymethyl)-2,5-dioxoimidazolidin-4-yl)-1,3-bis(hydroxymethyl)urea), cis-isomer of 1-(3-chloroallyl)-3,5,7-triaza-1-azoniaadamantane chloride (=Dowicil 200), 1-(3-chloroallyl)-3,5,7-triaza-1-azoniaadamantane chloride (=quaternium 15=Dowicil 100), DMDMH (=1,3-dimethylol-5,5-dimethylhydantoin). However, said formaldehyde donors are relatively expensive substances, the use of which for preserving technical mass-produced products is prohibited for reasons of cost alone.

DE-41 41 953 discloses microbicidal compositions which comprise, as active ingredients, a combination of at least one iodopropargyl derivative and benzyl alcohol mono(poly) hemiformal. Moreover, further compounds, e.g. formaldehyde or its donor substances or guanidine derivatives, can be added to the active ingredient combination.

U.S. Pat. No. 5,428,050 and U.S. Pat. No. 5,496,842 disclose a water-soluble preservative mixture which comprises powders of (a) one or more methylol compounds or equivalents thereof, and (b) iodopropynyl alcohol, its ester, carbamate or ether derivative, in a weight ratio of (a):(b) of from 100 to 2000:1. The patent specifications disclose the synergistic combination of (a) and (b). However, undesired formaldehyde emissions are not discussed.

DE-197 22 858 A1 relates to compositions based on iodopropynyl and formaldehyde donor compounds and use thereof as preservatives. Examples of formaldehyde donor compounds are N,N'-methylenebis(5-methyl-oxazolidine), 3,3'-methylenebis(tetrahydro-2H-1,3-oxazine) and 1-aza-5-ethyl-3,7-dioxabicyclo[3.3.0]-octane. The compositions of DE-197 22 858 A1 comprise iodopropynyl butylcarbamate as preferred iodopropynyl compound. As the IPBC content increases, the formaldehyde emissions increase, thus the biocidal effectiveness of the compositions in the gas phase also increases with increasing IPBC content. In the compositions, an addition of certain glycols has a positive influence on the odour of the compositions and reduces the emission of relatively volatile substances such as, for example, formaldehyde.

The use of compositions which comprise iodopropynyl compounds is thus precluded if particularly low formaldehyde emissions are desired, or in the case of use in environments which are incompatible with iodopropynyl compounds. Moreover, compositions which comprise iodopropynyl compounds have a tendency toward undesired discolorations.

The preservative of DE-40 26 756 A1 comprises a mixture of (a) an organic acid, (b) a monophenyl glycol ether and (c) a guanidine derivative. Further optional biocides mentioned are imidazolidineurea and/or hydantoin derivatives.

DE-199 61 621 A1 relates to compositions which comprise at least one bactericidal N-formal, at least one fungicide and at least one stabilizer. Particularly preferred formals are triazinetriethanol and N,N'-methylenebis(5-methyloxazolidine).

198 42 116 A1 discloses stable microbicidal compositions which comprise derivatives of methylene-bisoxazolidine and 1H-benzimidazol-2-ylcarbamic acid. Moreover, further active ingredients may be present, for example dimethylolurea, bis(hydroxymethyl)-5,5-dimethylhydantoin, diazolidinylurea, sodium hydroxyl-methylglycinate or diuron (1,1-dimethyl-3-(3,4-dichlorophenyl)urea. However, these substances are relatively expensive and/or toxic. Carbendazime(methyl 1H-benzimidazol-2-ylcarbamate) is regarded as undesired due to its toxic properties (cancerogenic, mutagenic, reproduction-toxic) and its classification as a toxic substance (from 0.1% use concentration), although it is difficult to replace due to its good microbicidal effect.

In addition, various technical products based on N/O-formal are known. Thus, for example, the reaction product of formaldehyde or paraformaldehyde and ethanolamine (Grotan BK=N,N',N"-tris(hydroxy-ethyl)hexahydrotriazine) has been used successfully as a preservative in the cutting fluid sector. Grotan BK is a colourless to slightly yellowish liquid with a characteristic odour. On the basis of legal provisions, it has become a requirement to label a preparation containing greater than or equal to 0.1% of hexahydro-triazine (labelling requirement from 0.1% of hexahydrotriazine as R 43). In practice, a labelling of such substances or preparations (e.g. cutting fluid emulsions) cannot be carried out. As alternatives, therefore, biocides are sought which do not lead to a corresponding labelling, but on the other hand are comparatively effective, cost-effective and are acceptable from organoleptic considerations. These biocides should not necessarily comprise a large amount of hexahydrotriazine, but at the same time can release a large amount of formaldehyde, based on the weight.

An alternative to Grotan BK which is used is, inter alia, the 1:1 condensation product of paraformaldehyde and isopropanolamine (N,N,N"-tris(β-hydroxypropyl)hexahydrotriazine, Grotan WS). Grotan WS is, due to the lower content of formaldehyde, somewhat less effective than Grotan BK, and is also more odour-intensive and significantly more expensive than Grotan BK.

For many years, a condensation product of paraformaldehyde and isopropanolamine (weight ratio 3:2, Mar 71 or Grotan OX or GrotaMar 71, N,N'-methylenebis(5-methyloxazolidine) has also been used. The commercial products are anhydrous or low-water, colourless to slightly yellowish liquids with a characteristic pungent odour reminiscent of amine and formaldehyde. The biocidal effectiveness is very good due to the comparatively high formaldehyde content. However, the odour is perceived as a disadvantage during use. In particular, the pungent odour reminiscent of formaldehyde and the formaldehyde emission have been criticized.

Although, as has been mentioned, it is known from DE 197 22 858 A1 that certain glycols have a positive influence on the odour of compositions which comprise formaldehyde donor compounds and can reduce the emission of relatively volatile substances such as formaldehyde, the addition of relatively large amounts of odour-modifying additive, however, reduces, in an undesired way, the active ingredient content, based on the total weight. At the same time, emissions of odour-modifying additive (solvent) automatically arise, these emissions are in turn undesired.

Preparations based on dimethyloldimethylhydantoin (DMDMH) or tetramethylolglycoluril are also known. Apart from the fact that DMDMH and tetramethylolglycoluril are relatively expensive, they are solids or aqueous preparations which are unsuitable for certain fields of application. For example, it is impractical if, in the preparation of a dilute cutting fluid, a solid additive has firstly to be dissolved. In addition, a water fraction often has an unfavourable effect on the (storage) stability of certain active ingredients. Aqueous preparations also often have inadequate low-temperature stability. Water automatically reduces a high formaldehyde content and has an unfavourable effect on the emission of volatile constituents.

An object of the present invention was consequently to provide a formaldehyde donor preparation as preservative for cutting fluid concentrates and cutting fluid emulsions, technical emulsions or as biocidal additive for products (e.g. diesel fuel) or in processes (e.g. in the offshore sector, boring fluids). This preparation should
1. be able to be formulated in a cost-effective manner,
2. release comparatively small amounts of formaldehyde into the gas phase,
3. be acceptable in terms of odour,
4. have a high content of formaldehyde which can be cleaved off, i.e. the preparation should not automatically have a high solvent content,
5. be storage-stable, even over a prolonged period,
6. be miscible with further known biocidal, anti-microbial active ingredients and functional additives or auxiliaries without incompatibilities arising,
7. be able to be formulated in various forms, i.e. as a solid, semisolid, pasty or liquid preparation, and
8. be able to be formulated on the basis of formaldehyde donor compounds on the market, so that no new approval proceedings are necessary.

According to the invention, it has now been found that this object is achieved by a preservative according to claim 1, which comprises a) at least one formal and b) at least one emission-reducing additive which is chosen from urea, urea derivatives, amino acids, guanidine and guanidine derivatives, where the preservative (i) comprises no iodopropynyl compound and (ii) no derivative of 1H-benzimidazol-2-ylcarbamic acid.

Preferred embodiments are the subject-matter of the dependent claims.

The formal used according to the invention is preferably a N- and/or O-formal. Examples of such formaldehyde donor compounds are N-formals which are a reaction product or condensation product of a mono- or polyhydric, amino-substituted $C_1$- to $C_{10}$-alkyl-, -aryl-, -aralkylalcohol and a formaldehyde-supplying compound, and/or O-formals which are reaction products of a mono- or polyhydric $C_1$- to $C_{10}$-alkyl-, -aryl-, -aralkylalcohol or a glycol or glycol ether and a formaldehyde-supplying compound.

Examples of O-formals are (ethylenedioxy)dimethanol, benzyl alcohol hemiformal, propylene glycol hemiformal and butyl diglycol hemiformal. Examples of N-formals are N,N',N''-tris(hydroxyethyl)hexahydrotriazine, N,N',N''-tris(β-hydroxypropyl)hexahydrotriazine, N-methylolchloroacetamide, cis-isomer of 1-(3-chloroallyl)-3,5,7-triaza-1-azoniaadamantane chloride, 1-(3-chloroallyl)-3,5,7-triaza-1-azoniaadamantane chloride, 5-(polyoxymethylene)-1-aza-3,7-dioxabicyclo[3.3.0]-octane, ({[1-methyl-2-(5-methyloxazolidin-3-yl)ethoxy]-methoxy}methoxy) methanol, 4,4-dimethyloxazolidine, 7a-ethyldihydro-1H,3H,5H-oxazolo[3,4-c]oxazole, 2-(hydroxymethylamino) ethanol, 1-(hydroxymethylamino)propan-2-ol and N,N'-methylenebis(5-methyloxazolidine). According to the invention, particular preference is given to N,N'-methylenebis(5-methyl-oxazolidine).

Examples of emission-reducing additives are chosen from glycoluril, tetramethylolglycoluril, dimethylhydantoin, dimethyloldimethylhydantoin, dimethylolurea, tetramethylolurea, imidazolidinylurea and diazolidinylurea. A particularly preferred emission-reducing additive is urea.

A compound which is covered by the definition of an emission-reducing additive is per definitionem no formal (a) for the purposes of the description of the present invention. The emission-reducing additive can thus itself be a formal (a formaldehyde donor compound) (such as tetramethylolurea) and thus reduce the necessary amount of formal (a), which is advantageous if the formal (a) is a hexahydrotriazine.

The preservative according to the invention can also comprise one or more odour-modifying additives, such as alcohols, glycols and glycol ethers, where phenoxy-ethanol, phenoxypropanols, benzyl alcohol, phenethyl alcohol, phenylpropanols, phenylbutanols and phenyl-pentanols are particularly suitable, particular preference being given to phenoxyethanol. A further preferred odour-modifying additive is majantol (phenylpentanol).

Moreover, the preservative can comprise one or more biocides, for example boric esters, boric acid salts, lactic acid derivatives, isothiazolones, pyridine derivatives, phenols and parabens.

Examples of further biocides which can be used according to the invention can also be found in the BPD (Biocidal Product Directive) list of active ingredients. The combination with these known biocides serves to extend the spectrum of activity and/or to achieve synergistic increases in activity. Particular preference is given to combinations with thiabendazol, 2-mercaptopyridine N-oxide derivatives, such as pyrion-Na, zinc pyrithione, isothiazolones, such as N-octylisothiazolone, 4,5-dichloro-N-octylisothiazolone, N-methylisothiazolone, kathon 886, benzisothiazolone, n-butylbenzisothiazolone, phenols, such as o-phenylphenol, parabens, thiophene compounds, such as N-cyclohexylbenzothiophene-2-carboxamide S,S-dioxide, amines, such as 2-amino-2-methylpropanol, quaternary ammonium salts such as benzalkonium chloride, didecyldimethylammonium chloride, Vantocil IB, aldehydes, such as glutardialdehyde and o-phthaldialdehyde, and also active oxygen compounds, such as tert-butyl hydroperoxide.

The preservative according to the invention can also comprise (e) one or more additives, for example solvents, solubility promoters, corrosion inhibitors, alkalinizing agents, dyes, perfume, viscosity-modifying agents, foam inhibitors, emulsifiers, and antioxidants, dispersants, complexing agents, wetting agents, cleaning components, surfactants, pigments, ethereal oils, lubricant additives, care additives, fillers and polymers. Preferably, the preservative according to the invention, however, comprises no hydrolyzable, polymeric resin.

A preferred embodiment of the invention relates to a preservative in which the weight ratio (a):(b) is in the range from 500:1 to 1:1, preferably 200:1 to 5:1, more preferably 100:1 to 10:1 and in particular 50:1 to 20:1. Odour-modifying additives may be present in amounts of from 0 to 20% by weight, preferably 1 to 10% by weight, particularly preferably 4 to 8% by weight, based on the total weight of the preservative. In a further embodiment, the odour-modifying additive can be present in an amount of 90% by weight or less, preferably 40% by weight or less and particularly preferably 20% by weight or less, based on the total weight of the preservative.

In a preferred embodiment, the preservative according to the invention consists of a) formal, b) emission-reducing additive and optionally c) odour-reducing additive and possibly a small amount of water (up to 10% by weight of water, preferably up to 5% by weight).

A further preferred embodiment relates to a preservative which comprises
a) 90 to 99% by weight, preferably 92 to 98% by weight, more preferably 93 to 97% by weight, in particular about 95% by weight, of N,N'-methylenebis(5-methyloxazolidine) and
b) 1 to 10% by weight, preferably 2 to 8% by weight, more preferably 3 to 7% by weight, in particular about 5% by weight, of urea,
for example a preservative which consists of these two components in said amounts.

A further preferred embodiment relates to a preservative which comprises
a) 80 to 98% by weight, preferably 84 to 96% by weight, more preferably 86 to 94% by weight, in particular about 90% by weight, of N,N'-methylenebis(5-methyloxazolidine),
b) 1 to 10% by weight, preferably 2 to 8% by weight, more preferably 2 to 7% by weight, in particular about 5% by weight, of urea and
c) 1 to 10% by weight, preferably 2 to 8% by weight, more preferably 3 to 7% by weight, in particular about 5% by weight, of phenoxyethanol,
for example preference is given to a preservative which consists of these three components in said amounts.

It is possible to formulate the preservative according to the invention by simply mixing component a) with component b) and optionally further constituents. However, a preferred preparation variant relates to a process in which
a) at least one amine and/or alcohol is initially introduced,
b) formaldehyde is added,
c) the mixture is optionally heated to a temperature in the range from 50° C. to 100° C.,
d) at least one emission-reducing additive is added which is chosen from urea, urea derivatives, amino acids, guanidine and guanidine derivatives,
e) the mixture is optionally heated to a temperature in the range from 50° C. to 100° C. and
f) optionally odour-modifying additive is added which is chosen from alcohols, glycols and glycol ethers.

Preferably, odour-reducing additive is only added shortly prior to the preservative being used.

In a preferred embodiment of the process according to the invention
the temperature of step c) is in the range from 60° C. to 80° C., in particular about 70° C., and
the temperature of step e) is in the range from 60° C. to 80° C., in particular about 70° C., and additionally in step e) water is distilled off under reduced pressure.

In this preferred embodiment, particularly low formaldehyde emissions are observed for the preservative thus prepared.

In addition, the invention relates to the use of a preservative according to the invention for preserving a technical product, such as a cutting fluid, propellant, surface coating, a dispersion or a water-based paint.

Moreover, the invention relates to the use of urea, urea derivatives, amino acids, guanidine or guanidine derivatives for reducing the formaldehyde emission of a composition which comprises a formal.

The preservatives according to the invention may be solid, semisolid, pasty or liquid, they are preferably liquid. In a further preferred embodiment, the preservatives have a low content of water, for example they comprise 10% by weight of water or less, preferably 5% by weight or less, in particular 1% by weight or less of water, particular preference being given to anhydrous preservatives.

The preservative according to the invention offers, inter alia, the following advantages:
it can be formulated in a cost-effective manner from standard commercial components,
it has a high formaldehyde content, but at the same time greatly reduces formaldehyde emissions (gas phase),
it can be formulated in diverse forms, for example in a mixture with further biocides,
it has good storage stability, the slight clouding or precipitates sometimes observed with pure liquid formals such as Grotan OX do not arise in the case of the preservative according to the invention,
through the addition of the emission-reducing additive it is possible to reduce the nonvolatile and volatile nitrosamines which form in small amounts in certain applications (e.g. as preservatives in cutting fluid emulsions),
upon storage in plastic containers, no neck-in effect arises, resulting in a cost saving (the plastic containers can be reused more often).

Formals are used to prevent microbial deposits on filters and in tank plants as fuel additive, also in modern speciality fuels which represent an emulsion of diesel fuel in water. An addition of urea to formal (such as N,N'-methylenebis(5-methyloxazolidine)) does not only reduce the emission of formaldehyde or formaldehyde donor compounds, but also brings about a reduction in the NO emission upon combustion of the propellant equipped with the preservative according to the invention.

These and further advantages are also evident from the examples below.

EXAMPLES

Grotan OX is N,N'-methylenebis(5-methyloxazolidine). Protectol 140 is tetramethylolacetylenediurea.

1. Method of Determining Formaldehyde in the Gas Phase
The determination of the formaldehyde content in the gas phase above various preservatives was carried out using Dräger tubes 0.2/a (No. 6733081) in accordance with the instructions for use from Dräger-Sicherheitstechnik GmbH (8th Edition, May 1999). For this purpose, about 100 g of the sample to be investigated were introduced into a 250 ml wide-necked beaker with a screw lid and left to stand, in the closed state, for at least three hours at room temperature. The measurement was read off after two strokes on the scale 0.5 to 5 ppm, n=10. The measurements were carried out under comparable external conditions. Although the measurement results do not indicate an absolutely exact value in ppm of formaldehyde, the method is highly suitable for differentiating the formaldehyde emissions of different samples.

2. Method of Determining Formaldehyde in the Liquid Phase

Basis: The formaldehyde to be determined is expelled from the matrix using steam distillation (steam distillation apparatus according to Antona). The steam/formaldehyde mixture is passed over a distillation bridge and condenses on a high-efficiency condenser. The condensate is collected in a measuring flask. One aliquot fraction of this water/formaldehyde mixture is reacted. The formaldehyde condenses with 2,4-pentanedione in the presence of ammonium salts to give 3,5-diacetyl-1,4-dihydrolutidine. The resulting 3,5-diacetyl-1,4-dihydrolutidine is bright yellow in colour. Following an upstream steam distillation, apart from acetaldehyde in excess, no undesired substance is known.

Formaldehyde reagent: 75.0 g of ammonium acetate p.a. 1.5 ml of glacial acetic acid p.a. 1.0 ml of acetylacetone (2,4-pentanedione) for spectroscopy=>made up with demineralized water (demin. water) to 500 ml (volumetric flask)

Procedure: The size of the initial weight is governed by the formaldehyde content to be expected in the sample. Subsequent steam distillation is carried out to a value of 100 ml (or 250 ml). The formaldehyde content in the distillate should be 0.10 mg/l to 0.2 mg/l, so that 5-20 ml of the distillate can be reacted. In the case of water-soluble samples with a higher formaldehyde content (no direct distillation possible), a corresponding initial weight is weighed into a 100 ml volumetric flask and made up with demin. water. 5 to 10 ml of this solution are used for the reaction. In the case of water-insoluble samples, the initial weight is rinsed over with demin. water into the Antona charge, or it is weighed directly into the charge. The sample to be distilled is treated with 10 ml of 20% strength sulphuric acid (depending on the objective, a neutral or alkaline distillation is also possible). To check the quantitative distillation, after the intended volume has been distilled off, additionally about 1 ml of distillate can be tested with 1 ml of formaldehyde reagent in the beaker with warming with regard to a formaldehyde reaction.

2 to 20 ml of the distillate (100 ml or 250 ml) are placed in a 25 ml volumetric flask and treated with 5 ml of formaldehyde reagent and made up to 25 ml with demin. water. The flask is placed into a waterbath at 40° C. for 30 mins. After cooling to room temperature, the absorbance of the solution is measured in 1 cm glass cells in a UV photometer at 412 nm against a blank (blank: 5 ml of formaldehyde reagent are made up to 25 ml with demin. water and also heated at 40° C. for 30 minutes).

Evaluation: The formaldehyde samples are evaluated against a formaldehyde calibration curve on the UV photometer.

Calibration curve: The calibration curve is constructed by appropriate initial weighing and dilution of the 37% formaldehyde solution, steam distillation not being required. The solutions for the calibration curve are added to 25 ml volumetric flasks, treated with 5 ml of formaldehyde reagent and made up with demin. water. The flasks are placed into a waterbath at 40° C. for 30 minutes and, after cooling to room temperature, measured against a blank at 412 nm.

3. Method of Preparing Preservatives According to the Invention

Method A

The preservative was formulated by simple mixing of formal with emission-reducing additive. The mixture was stirred until a clear solution was formed. If necessary, the solution was filtered. The odour of the preservative is significantly improved compared to Grotan OX, in particular the pungent formaldehyde odour is greatly reduced, the odour impression corresponds more closely to that of isopropanolamine.

Method B

Corresponds to method A, except that the mixing is carried out with heating.

Method C 901.3 g (12 mol) of 2-hydroxypropylamine were initially introduced and 592.0 g (12 mol) of paraformaldehyde (91.3% strength) were introduced with stirring such that 70° C. was not exceeded. When the addition was complete, the mixture was further stirred for 2 hours at 70° C. 46.5 g of urea were then added and water (in total 365 g) was distilled off under reduced pressure at 70° C. The mixture was filtered in order to produce a colourless liquid. The efflux time of a preservative prepared in this way from a DIN beaker 4 mm is 140 seconds at 20° C. (compared with Grotan OX 22 seconds). The efflux time from the DIN beaker 6 mm is 13 seconds at 20° C. (Grotan OX 6 seconds). The pH, as a 1% strength solution in demineralized water, is 10.5, the formaldehyde content is 45.3% by weight, the isopropanolamine content is 76.3% and the water content is 0.3% by weight. The formaldehyde content in the gas phase is less than 0.5 ppm (Grotan OX 3 to 5 ppm).

4. Determination of the Formaldehyde Emissions of Preservatives

In the gas phase of preservatives formulated as described, using the method described under 1., the following formaldehyde concentrations were measured in the gas phase (Table 1):

| No. | Constituent | % by wt. | Preparation process (stirring conditions) | HCHO content in the gas phase Blank | HCHO content in the gas phase 1 month |
|---|---|---|---|---|---|
| 1 | Grotan OX | 100 | — | 3-5 | 3 |
| 2 | Grotan OX Protectol 140 | 50 50 | A | >>5 | >>5 |
| 3 | Groton OX demineralized water | 90 10 | A | >>5 | >>5 |
| 4 | Grotan OX urea | 95 5 | B | 1-2 | 1-2 |
| 5 | Grotan OX urea water | 90 5 5 | A | 3-5 | 3-5 |
| 6 | Grotan OX urea phenoxyethanol | 90 5 5 | B | 1-2 | 1-2 |
| 7 | Grotan OX urea | 98 2 | A (1 day) | 2-3 | 3 |
| 8 | Grotan OX urea | 96 4 | A (3 days) | 0.5-1 | 1-2 |

-continued

| No. | Constituent | % by wt. | Preparation process (stirring conditions) | HCHO content in the gas phase | |
|---|---|---|---|---|---|
| | | | | Blank | 1 month |
| 9 | Grotan OX urea | 96 4 | B (70° C., 2 h) | 0.5-1 | 1 |
| 10 | Grotan OX urea | 96 4 | C | 0 | 0 |
| 11 | Grotan OX 5,5-dimethylhydantoin | 96 4 | A | 0.5 | |

Table 1 shows that the formaldehyde content in the gas phase of a water-containing preservative (No. 3) is significantly increased compared to Grotan OX (No. 1), this increase can be compensated by adding urea (No. 5). In anhydrous formulations, the formaldehyde content in the gas phase is significantly and permanently reduced from a urea content of about 2% by weight. However, since in the case of a content of 4% by weight of urea or more, it is necessary to stir either for 3 days at room temperature or for 2 hours at 70° C. in order to obtain a completely homogeneous mixture, it is advantageous to add the urea during the preparation of Grotan OX, specifically after the reaction between alkanolamine (2-hydroxypropylamine) with formaldehyde is complete, and before the water is distilled off (process C).

The invention claimed is:

1. A method of reducing the formaldehyde emissions of a composition comprising a formal, comprising: adding at least one component to a composition comprising at least one formal, wherein the at least one component is selected from the group consisting of: urea, urea derivatives, amino acids, guanidine and guanidine derivatives and wherein the at least one formal is selected from the group consisting of an N-formal, an O-formal and a combination thereof.

2. The method according to claim 1, wherein the at least one component is a urea derivative and the urea derivative is selected from the group consisting of: glycoluril, tetramethylolglycoluril, dimethylhydantoin, dimethyloldimethylhydantoin, dimethylolurea, tetramethanolurea, imidazolidinylurea, and diazolidinylurea.

3. The method according to claim 1, wherein the at least one formal is an O-formal selected from the group consisting of dimethanol, benzyl alcohol hemiformal, propylene glycol hemiformal, and butyl diglycol hemiformal.

4. The method according to claim 1, wherein the at least one formal is an N-formal selected from the group consisting of:
N,N',N''-tris(hydroxyethyl)hexahydrotriazine,
N,N',N''-trisβ-hydroxypropyl)hexahydrotriazine, and
N,N'-methylenebis(5-methyloxazolidine).

5. The method according to claim 1, wherein the at least one component is added to the composition in an amount so that the weight ratio of said at least one formal to said at least one component is 500:1 to 1:1.

6. The method according to claim 4, wherein the weight ratio of said at least one formal to said at least one component is 200:1 to 5:1.

* * * * *